US00PP08309P

United States Patent [19]

Vletter

[11] Patent Number: Plant 8,309

[45] Date of Patent: Jul. 20, 1993

[54] LILY PLANT NAMED BELCANTO

[75] Inventor: Floris Vletter, Rijnsburg, Netherlands

[73] Assignee: Gebr. Vletter & J. A. Den Haan, Rijnsburg, Netherlands

[21] Appl. No.: 796,532

[22] Filed: Nov. 21, 1991

[51] Int. Cl.[5] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new and distinct cultivar of lily plant named Belcanto, characterized by its large flowers, floriferous habit, soft pink flower color, orange pollen, and numberous spot markings which are cherry red in color.

1 Drawing Sheet

The present invention comprises a new and distinct cultivar of lily, botanically known as Lilim, known commercially as Lilium oriented hybrid, and hereinafter referred to by the cultivar name Belcanto. The parents were oriental varieties belonging to division VII(b) described in "Classification of Lily Cultivars into Divisions" published by Victoria Mathews, The Royal Botanic Gardens, Kew (1989).

The new cultivar is a product of a planned breeding program which had the objective of creating new lily cultivars having large flowers, solid stems, characteristics that collectively meet the requirements of production of cut-flowers, and soft pink flower color.

The new cultivar was originated from a hybridization made by the inventor in a controlled breeding program in Rijnsburg, The Netherlands in 1983. The female parent was an unknown seedling, and its male parent is an unnamed seedling.

The new cultivar was discovered and selected as one flowering plant within the progeny of the stated cross by the inventor in July 1983 in a controlled environment in Rijnsburg, The Netherlands.

The first act of asexual reproduction of the new cultivar was accomplished by the inventor when scales where taken from the initial selection in 1987 in a controlled environment in Rijnsburg, The Netherlands.

Horticultural examination of selected units has demonstrated that the combination of characteristics as herein disclosed for the new cultivar are firmly fixed and are retained through successive generations of asexual reproduction.

The new cultivar has not been observed under all possible environmental conditions. The phenotype may vary somewhat with variations in environment such as temperature, light intensity, and day length, without, however, varying in the genotype. The following observations, measurements and comparisons described plants grown in Wageningen and Rijnsburh, The Netherlands under greenhouse conditions which approximate those generally used in commerical practice.

The following traits have been repeatedly observed and are determined to be basic characteristics of the new cultivar which in combination distinguish Belcanto as a new and distinct cultivar.

1. Large flowers and floriferous habit;
2. A rather horizontal flower position for oriental hydrids;
3. Light, soft pink flower color;
4. Constrasting orange pollen;

5. Numerous cherry red spot makrings;

Of the many cultivars known to the present inventor, the most similar in comparison to the new cultivar is Acapulco, disclosed in a pending application of applicant. In comparison to Acapulco, Belcanto has larger flowers, lighter pink flower color, its flowers are more horizontal, and it produces more flowers in relation to bulb size. When flowering is forced under natural light, Belcanto produces flowers approximately 4 days earlier than Stargazer, grown under the same conditions. Belcanto is fertile.

The accompanying photographic drawing shows typical flower characteristics of the new cultivar, with colors being as true as possible with illustrations of this type. The photo is a front elevational view showing several open flowers and buds at varying stages.

In the following description, color references are made to The Royal Horticultural Society (R.H.S.) Colour Chart. The colour values were determined at Wageningen in 1989–1990 and at Rijnsburg in July 1991.

Origin: Seedling from Breeding Program.

Parentage:

*Seed parent.*—Unknown seedling.

*Pollen parent.*—Unnamed seedling.

Classification:

*Botanical.*—Lilum.

Commerical.—Oriental hybrid.

THE PLANT

Form: A single stem carrying numerous pedicels alternately arranged.

Height: Approximately 140 cm at time of opening of anthers of first flower.

Growth habit: Vigorous.

Stem: Circular in transverse section; color R.H.S. 144A; internodal length 2 cm and uniform; anthocyanin pigmentation present.

Foliage:

*Quantity.* 55–65 leaves, depending on growing conditions.

*Size of leaf.*—Mature leaves are short to medium in length (18 cm), and medium in width (3 cm).

*Shape of leaves.*—Ovate.

*Texture.*—Smooth with weak glossiness on upper side.

*Color.*—Medium green 137A.

Bulbs:

*Size.*—Outlet 6–30 cm.

*Color.*—White, purple and yellow.
Roots: Both stem and contractile presnet.

THE BUD

Form: Tapering (like a lancet).
Size: 10 cm prior to opening.
Opening: Unfolds normally.
Color: 75B (Color prior to opening).
Tepals: Folded, three visible.

THE FLOWER

Blooming habit: Raceme.
Size: 19 cm diameter, depending somewhat on growing conditions.
Borne: Horizontal.
Shape: Generally in form of hexagonal star, and bowl shaped in cross-section.
Tepalage:
*Number of tepals.*—Six.
*Arrangement.*—Three inner and three outer each with marginal undulatin.
*Color.*—Upper surface: Light pink 69B. Lower surface: White 155B with shade of light pink.
*Spotting or marking*—Cherry red spots of 0.5–1.5 mm diameter, approximately 60 in number; yellow to green colored strip at base of each tepal.

Pedical:
*Length.*—10 cm (first flower).
*Color.*—Medium green.
Texture: Papillose.
Disease resistance: No disease problems noted to date.
Fragrance: Present; medium strong.
Lasting quality: Excellent.

REPRODUCTIVE ORGANS

Stamens, anthers:
*Arrangement.*—Anthers form a genrally circular pattern.
*Length.*—Short to medium (8 cm).
*Number.*—Six.
*Filaments.*—Green.
Pollen color: Orange.
Anther color: Reddish brown.
Pistils: Green style; total length of pistil is 11 cm.
Stigma: Triangular and green stigma.
Ovaries: Triangular in shape other characteristics typical of oriental lily varieties.

I claim:

1. A new and distinct cultivar of lily plant named Belcanto, as illustrated and described.

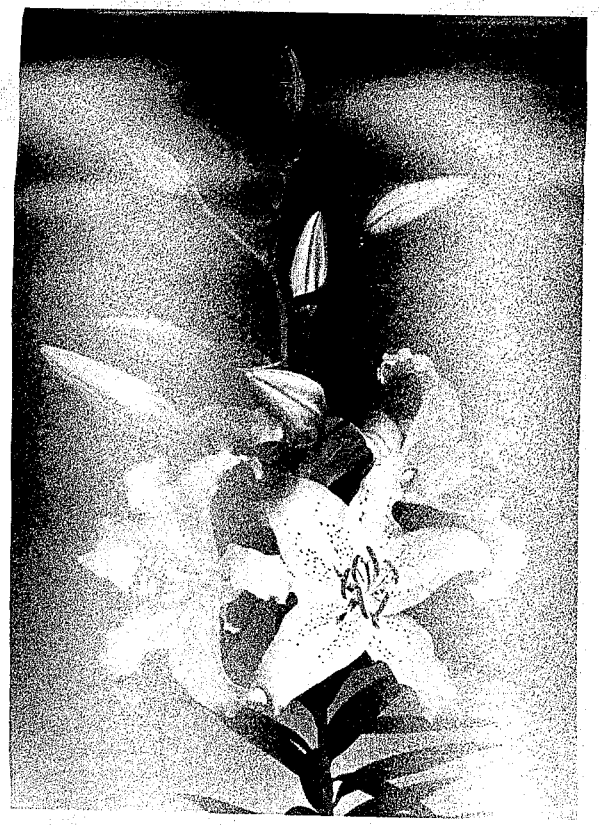

* * * * *